United States Patent
Hansen

(10) Patent No.: US 12,201,547 B2
(45) Date of Patent: Jan. 21, 2025

(54) METHOD OF PROVIDING A SIGNAL TO ALERT AN OSTOMATE OF AN IMMINENT LEAKAGE OF STOMA FLUIDS

(71) Applicant: Coloplast A/S, Humlebaek (DK)

(72) Inventor: Kristoffer Hansen, Naerum (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/222,530

(22) Filed: Jul. 17, 2023

(65) Prior Publication Data

US 2023/0355422 A1 Nov. 9, 2023

Related U.S. Application Data

(63) Continuation of application No. 16/324,909, filed as application No. PCT/DK2017/050259 on Aug. 9, 2017, now Pat. No. 11,744,725.

(30) Foreign Application Priority Data

Aug. 12, 2016 (DK) .................... PA 2016 70619

(51) Int. Cl.
*A61F 5/44* (2006.01)
*A61F 5/443* (2006.01)

(52) U.S. Cl.
CPC .......... *A61F 5/4404* (2013.01); *A61F 5/443* (2013.01)

(58) Field of Classification Search
CPC .......... A61F 5/4404; A61F 5/443; A61F 5/44; A61F 13/42; A61L 15/56; A61L 15/60; A61L 15/42; Y10S 252/964
See application file for complete search history.

(56) References Cited

U.S. PATENT DOCUMENTS

| | | | |
|---|---|---|---|
| 3,713,445 A | 1/1973 | Marsan | |
| 4,573,984 A | 3/1986 | Benzies | |
| 5,298,392 A | 3/1994 | Atlas et al. | |
| 5,607,413 A * | 3/1997 | Holmberg | A61F 5/448 |
| | | | 604/338 |
| 5,821,546 A | 10/1998 | Xiao et al. | |
| 5,861,270 A | 1/1999 | Nelis | |
| 5,942,186 A | 8/1999 | Sanada et al. | |
| 6,093,869 A | 7/2000 | Roe et al. | |
| 6,160,198 A | 12/2000 | Roe et al. | |
| 6,171,289 B1 | 1/2001 | Millot et al. | |
| 6,186,991 B1 | 2/2001 | Roe et al. | |
| 6,384,296 B1 | 5/2002 | Roe et al. | |
| 6,395,955 B1 | 5/2002 | Roe et al. | |
| 6,407,308 B1 | 6/2002 | Roe et al. | |
| 6,423,044 B1 | 7/2002 | Roe et al. | |
| 6,511,819 B2 | 1/2003 | Tryland et al. | |
| 6,570,053 B2 | 5/2003 | Roe et al. | |
| 6,713,660 B1 | 3/2004 | Roe et al. | |

(Continued)

FOREIGN PATENT DOCUMENTS

CA  1314248 C  3/1993
CA  2347436 A1  5/2000

(Continued)

*Primary Examiner* — Kai H Weng
*Assistant Examiner* — Alessandro R Del Priore
(74) *Attorney, Agent, or Firm* — Coloplast Corp., Coloplast A/S; Nick Baumann

(57) ABSTRACT

A method of providing a signal to alert an ostomate of an imminent leakage of stoma fluids relative to their ostomy device is disclosed.

12 Claims, 3 Drawing Sheets

(56) References Cited

U.S. PATENT DOCUMENTS

| | | |
|---|---|---|
| 6,802,808 B2 | 10/2004 | Brady |
| 7,118,870 B2 | 10/2006 | Field et al. |
| 7,777,092 B2 | 8/2010 | Lykke et al. |
| 7,858,839 B2 | 12/2010 | Elliott |
| 7,982,088 B2 | 7/2011 | Roe et al. |
| 8,048,644 B1 | 11/2011 | Steck et al. |
| 8,148,511 B2 | 4/2012 | Noble et al. |
| 8,178,340 B2 | 5/2012 | Clermont et al. |
| 8,319,003 B2 | 11/2012 | Olsen et al. |
| 8,740,865 B2 | 6/2014 | Krystek et al. |
| 9,066,812 B2 | 6/2015 | Edvardsen et al. |
| 9,068,976 B2 | 6/2015 | Putnam et al. |
| 9,078,764 B2 | 7/2015 | Davies et al. |
| 9,216,104 B2 | 12/2015 | Thirstrup et al. |
| 2003/0004477 A1* | 1/2003 | Nielsen ............... A61F 5/443 604/336 |
| 2005/0038380 A1 | 2/2005 | Nemir et al. |
| 2005/0064444 A1 | 3/2005 | Beimfohr et al. |
| 2005/0101841 A9 | 5/2005 | Kaylor et al. |
| 2007/0072174 A1 | 3/2007 | Sayler et al. |
| 2007/0122831 A1 | 5/2007 | Bachoon |
| 2007/0196884 A1 | 8/2007 | Bodini et al. |
| 2009/0298051 A1 | 12/2009 | Salter et al. |
| 2010/0204665 A1* | 8/2010 | Stroebech ............... A61F 5/445 604/344 |
| 2011/0182827 A1 | 7/2011 | Fuisz et al. |
| 2011/0256576 A1 | 10/2011 | Bissonnette et al. |
| 2012/0143154 A1 | 6/2012 | Edvardsen et al. |
| 2012/0143155 A1 | 6/2012 | Edvardsen et al. |
| 2012/0190025 A1 | 7/2012 | Blackwood et al. |
| 2012/0264637 A1 | 10/2012 | Wiener-Kronish et al. |
| 2013/0231620 A1* | 9/2013 | Thirstrup ............... A61F 5/445 604/344 |
| 2013/0296813 A2 | 11/2013 | Park |
| 2014/0081225 A1 | 3/2014 | Bourke |
| 2014/0186880 A1 | 7/2014 | Lowenkamp, Jr. |
| 2014/0292520 A1 | 10/2014 | Carney et al. |
| 2015/0368695 A1 | 12/2015 | Shanks et al. |
| 2016/0008182 A1 | 1/2016 | Prokopuk et al. |

FOREIGN PATENT DOCUMENTS

| | | |
|---|---|---|
| CN | 101698873 A | 4/2010 |
| CN | 102260744 A | 11/2011 |
| CN | 104846113 A | 8/2015 |
| DE | 102011014321 A1 | 9/2012 |
| EP | 1091719 B1 | 8/2003 |
| EP | 1091772 B1 | 12/2003 |
| EP | 1093352 B1 | 3/2004 |
| EP | 1091720 B1 | 5/2004 |
| EP | 1091773 B1 | 2/2007 |
| GB | 2431239 A | 4/2007 |
| JP | 2010172852 A | 8/2010 |
| JP | 5219861 B2 | 6/2013 |
| JP | 2014033745 A | 2/2014 |
| WO | 1996007755 A2 | 3/1996 |
| WO | 2000000137 A2 | 1/2000 |
| WO | 2000000151 A1 | 1/2000 |
| WO | 2000000233 A1 | 1/2000 |
| WO | 2000025836 A1 | 5/2000 |
| WO | 2000040182 A1 | 7/2000 |
| WO | 2000079497 A1 | 12/2000 |
| WO | 2002073154 A2 | 9/2002 |
| WO | 2007115590 A1 | 10/2007 |
| WO | 2015014774 A1 | 2/2015 |
| WO | 2015071315 A1 | 5/2015 |

* cited by examiner

METHOD OF PROVIDING A SIGNAL TO ALERT AN OSTOMATE OF AN IMMINENT LEAKAGE OF STOMA FLUIDS

SUMMARY

The disclosure relates to an ostomy appliance as defined in the appended claims. Particularly, the disclosure relates to such an appliance capable of predicting, or predetermining, leakage or potential leakage of stomal fluids and of giving a user or health care professional a warning in time to react before leakage occurs.

BACKGROUND

Leakage of stomal fluids continues to be a primary subject of concern for ostomists, often being referred to as a major contributor to reduced quality-of-life for this group of people.

However, even when leakage does not occur, all ostomy appliances eventually need to be changed. A normal maximum wear time for ostomy appliances is usually around 4-5 days. Over such a period of time, the adhesive interface with the skin is gradually weakened and the adhesive interface eventually fails. The reasons for this failure include moisture uptake from the skin to the adhesive material and the exposure of the adhesive material to the harsh stomal fluids.

One major issue in regards to leakage is that it often occurs unexpectedly and without any prior warning signals. Experience shows that leakage incidents can be caused by several factors, including factors which are unique to the individual user, such as the stoma type, location of stoma, peristomal skin topography and general health condition of the user. Most often, a leakage incident means that stomal fluids enter into a space between the proximal surface of the carrier sheet and user's skin. This leads to destruction and/or weakening of the adhesive material carrying the weight of the appliance, in many cases very rapidly and only detectable for the user once the failure has occurred and the damage done.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
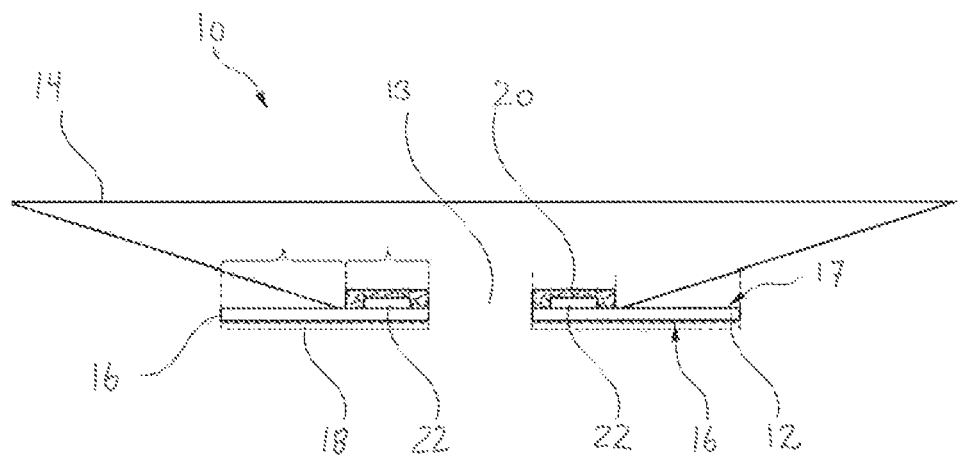
FIG. 1 illustrates a cross-sectional view of one embodiment of an ostomy appliance.

In this disclosure, whenever referring to proximal surface of a device or part of a device, the referral is to the skin-facing surface, when the wafer or ostomy appliance is worn by a user. Likewise, whenever referring to the distal surface of a device or part of a device, the referral is to the surface facing away from the skin, when the wafer or ostomy appliance is worn by a user. In other words, the proximal surface is the surface closest to the user, when the wafer is fitted on a user and the distal surface is the opposite surface—the surface furthest away from the user in use.

In this disclosure, "peristomal skin surface" is intended to mean a portion of an ostomist's skin surface immediately adjacent to and/or surrounding the ostomy.

In this disclosure, "dissipate" and "dissipation" is intended to refer to a gradual, stepwise or constant dissolving or breakdown process of a material. In other words, the depletion of a material over time, either in stages of different intensity or at a relatively constant rate.

In this disclosure, the wordings "ostomy" and "stoma" are used interchangeably without any intent to imply different meanings.

In this disclosure, "stomal fluids" is intended to mean output from a stoma, being faeces and/or urine in a more or less viscous form or mucins secreted from the epithelial layer of the alimentary canal. In the case of a colostomy, the output may be quite solid, whereas an ileostomy may produce more liquid output. The output may contain digestive juices with enzymes and other components that can be aggressive to the skin and therefor can cause maceration of skin subjected to the output as well as to the materials of the ostomy appliance, including the adhesive material.

In this disclosure, "sheet" is intended to mean a thin, flat piece of material.

In this disclosure, "swellable" is intended to mean the capability of a material to take up moisture or liquid/fluid leading to an increase in the volume of the material. The volume increase can be substantial, such as to be visible to the naked eye without problem or by being easily felt by a user of the ostomy appliance.

Embodiments provide an ostomy appliance comprising a carrier sheet having an adhesive material on a proximal surface for attachment to the skin surface of a user, the appliance further comprising a second material on a distal surface of the carrier sheet and a signal generator adapted to provide an indicator signal in response to dissipation of the second material caused by exposure to stomal fluids acting on a side of the carrier sheet facing away from the skin of user. Embodiments further provide such an appliance comprising a collecting bag for collecting stomal fluids. Embodiments further provide such an appliance wherein the collecting bag is permanently or detachably connected to the carrier sheet.

Embodiments provide an ostomy appliance that is capable of providing an indicator signal to the user warning him/her of an imminent leakage incident or the potential therefor. Unlike existing solutions, the ostomy appliance of the present disclosure provides a solution which reacts to the breakdown or depletion of a second material that is not critical to maintaining the function of the appliance.

The breakdown of such non-critical, second material occurs as a result of the second material being exposed to stomal fluids. The breakdown of the second material happens on the side of the carrier sheet facing away from the user. A preferred level of breakdown of the second material, at which the indicator signal is set off, can be selected and made to reflect or mimic a breakdown-level of the first adhesive material, at which the breakdown of the first adhesive material is not yet critical for the correct functioning of the appliance. In other words: according to the present disclosure a warning in due time before the occurrence leakage. As such, the preferred breakdown-level of the second material can be set to correspond to a level of breakdown of the load-carrying first adhesive material.

The breakdown-levels of the first adhesive material and the second material can be based on experience and/or test generated data. One way of obtaining such data is by testing and correlating the breakdown-time and/or breakdown—manner of adhesive material of the type disposed on the proximal surface of the carrier sheet with the breakdown-time and/or breakdown—manner of the second material of the type disposed on the distal surface of the carrier sheet.

Based on such data, a preferred breakdown-level of the second material on the distal surface of the carrier sheet can be chosen such that it corresponds to certain, not yet critical breakdown-level of the first adhesive material. As the signal generator is adapted to set off an indicator signal when the dissipation of the second material has reached a preferred level, the user is provided with a warning in time to change to a new appliance before the old appliance fails and leakage occurs. The present disclosure thus relates to an ostomy appliance which is capable of predicting, or predetermining, leakage or potential leakage and warn a user in time to react before the leakage occurs.

FIG. 1 is a cross-sectional view illustrating one embodiment of an ostomy appliance 10 of the present disclosure comprising a carrier sheet 12, a first adhesive material 18, a second material 20 and a signal generator 22. The carrier sheet 12 has a proximal surface 16 and a distal surface 17. The first adhesive material 18 is disposed on the proximal surface 16 of the carrier sheet 12. The second material 20 is disposed at least on a portion of the distal surface 17 of the carrier sheet 12. A through-going hole 13 extends from the proximal surface 16 of the carrier sheet 12 to the distal surface 17 of the carrier sheet 12. A first zone 26 is configured radially inward of an attachment between the collecting bag 14 and the distal surface 17 of the carrier sheet 12 in relation to the through-going hole 13, and a second zone 28 is configured radially outward of the attachment. In embodiments, the second material 20 and the signal generator 22 are located in the first zone 26. Thereby, stomal fluid exiting the stoma is prevented from coming into contact with the distal surface 17 of the carrier sheet 12 in the second zone 28. In embodiments, no portion of the second material 20 is provided radially outward of the attachment between the collecting bag 14 and the distal surface 17 of the carrier sheet 12, i.e. no portion of the second material 20 is located in the second zone 28. Embodiments ensure that only the first zone 26 can be exposed to stomal fluids, thereby providing for the flow of stomal fluids to be directed to the second material 20.

Figure 2:
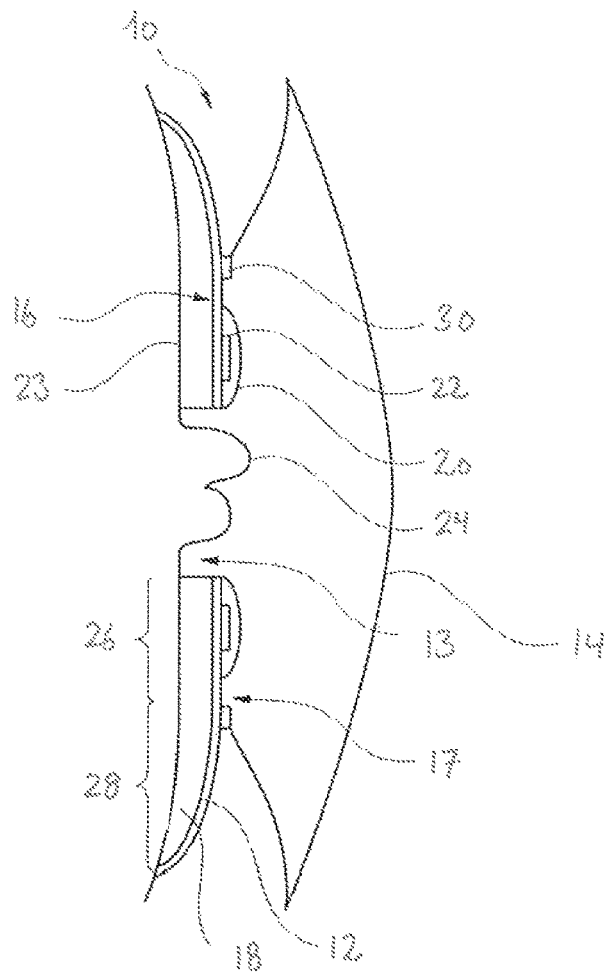
FIG. 2 illustrates a cross-sectional view of one embodiment of an ostomy appliance.

FIG. 2 is a cross-sectional view illustrating one embodiment of an ostomy appliance 10 of the present disclosure in a use-situation where it is located on the skin surface 23 and around the stoma 24 of a user.

Figure 3:
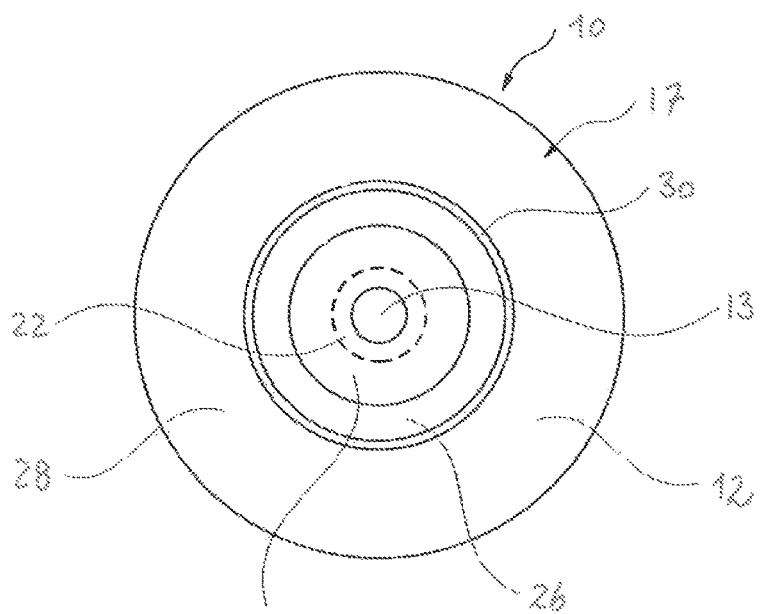
FIG. 3 illustrates a top view of one embodiment of an ostomy appliance.

FIG. 3 is a top view of one embodiment of the ostomy appliance 10 of the present disclosure with the collection bag 14 left out for illustration purposes. The view illustrates the appliance 10 with the distal surface 17 of the carrier sheet 12 facing the viewer. The embodiment shows the signal generator 22 in dotted line, to illustrate that in a prior-to-use condition of the appliance 10, as shown in FIG. 3, the signal generator 22 is covered by the second material 20. In the embodiment of FIG. 3, the signal generator 22 is illustrated as being applied in a ring shape.

In one embodiment, the signal generator 22 is provided between the distal surface 17 of the carrier sheet 12 and the second material 20. In one embodiment, the second material 20 is configured to enclose the signal generator 22 on three sides while the distal surface 17 of the carrier sheet 12 encloses the signal generator 22 on a fourth side. In one embodiment, the second material 20 is configured to cover the signal generator 22 on one side. In one embodiment, the second material 20 is configured to cover the signal generator 22 on two sides. In one embodiment, the second material 20 is disposed directly onto the distal surface 17 of the carrier sheet 12. In one embodiment, the signal generator 22 is provided between distal surface 17 of the carrier sheet 12 and the second material 20, such that less than an entirety of the second material 20 is disposed directly on the distal surface 17 of the carrier sheet 12. In one embodiment, the signal generator 22 is attached to the distal surface of the carrier sheet 12.

Figure 4:
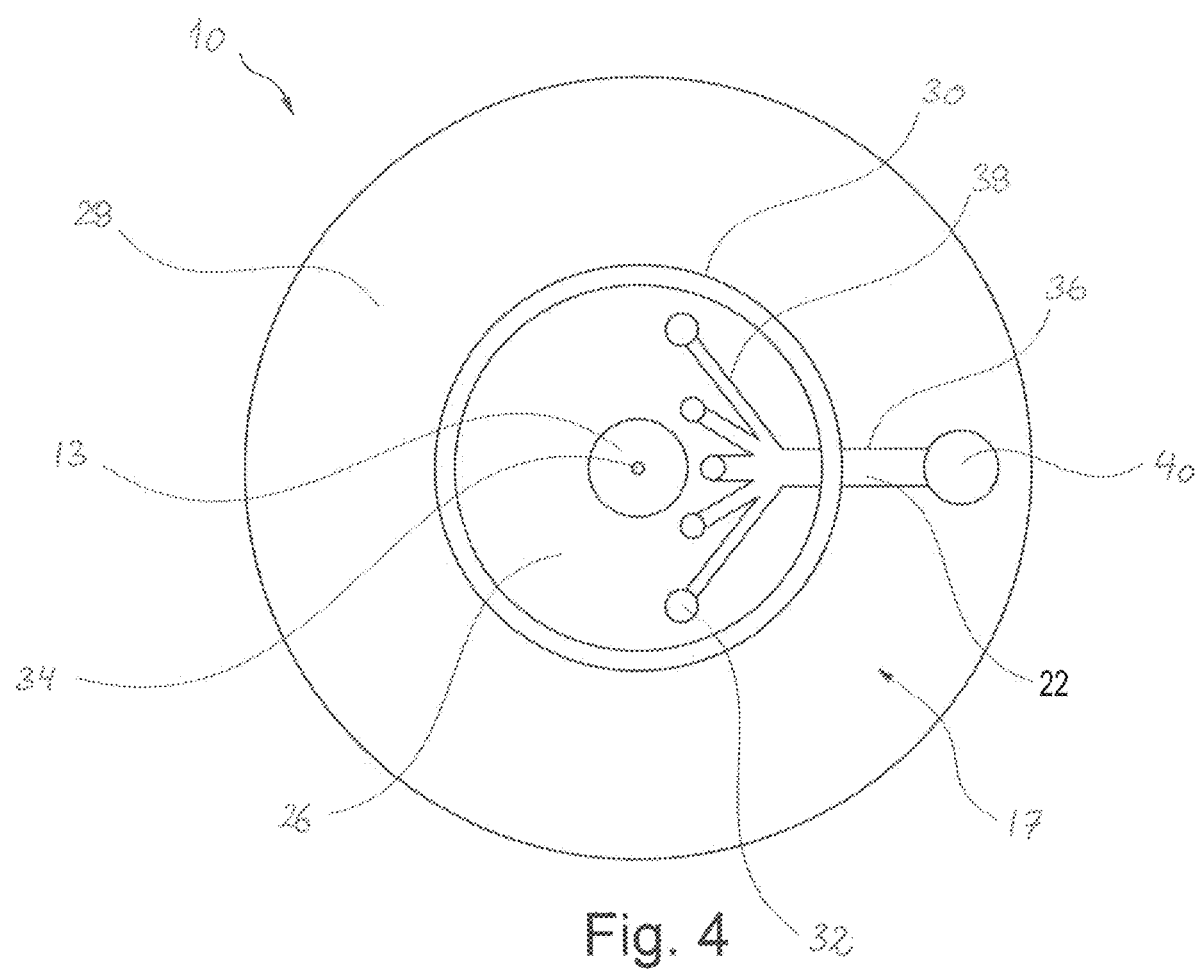
FIG. 4 illustrates a top view of one embodiment of an ostomy appliance.

FIG. 4 schematically illustrates a top view of one embodiment, in which the signal generator 22 comprises a plurality of dot-formed attachment portions 32 on the distal surface 17 of the carrier sheet 12. In FIG. 4, the collecting bag 14 and the second material 20 are left out for illustration purposes. In one embodiment, the plurality of dot-formed attachment portions 32 locates in a first zone 26 radially inward of an attachment 30 of the collecting bag 14 to the distal surface 17 of the carrier sheet 12, when seen in relation to a central longitudinal axis 34 extending through the through-going hole 13. In one embodiment, each of the dot-formed attachment portions 32 is individually connected to a primary portion 36 of the signal generator 22. In one embodiment, the individual connections 38 between the dot-formed attachment portions 32 and the primary portion 36 takes a shape similar to a treetop wherein the dot-formed attachment portions 32 are the branches and the primary portion 36 the trunk of the tree. Alternatively, the individual connections between the dot-formed attachment portions and the primary portion forms a shape comparable to an open palm of a hand and forearm. In one embodiment, the signal generator 22 is located on the distal surface 17 such that it extends radially from the first zone 26 to the second zone 28 and under the collection bag attachment 30. In embodiments, two or more signal generators 22 are provided. Thereby, leakage can be detected in a plurality of locations providing secure and fast detection.

The different distributions of the second material 20 in relation to the signal generator 22 according to the several embodiments provide additional options for selecting a predetermined breakdown-level of the second material 20, at which the signal generator 22 is adapted to set off an indication signal to warn the user about potential, or upcoming, leakage.

In one embodiment, a portion of the second material 20 being radially closest to a central, longitudinal axis extending through the through-going hole 13, is adapted to be flush (at level or in line) with a periphery of the through-going hole 13 in the carrier sheet 12. In one embodiment, the portion of the second material 20 being radially closest to the central, longitudinal axis extending through the through-going hole 13, is adapted to be offset from the periphery of the through-going hole 13 in the carrier sheet 12 in relation to the central, longitudinal axis. Effects of offsetting the radially innermost portion of the second material 20 include the provision of an ostomy appliance that allows to customize the size and shape of the through-going hole 13 in order to receive an individual, unique stoma.

In one embodiment, the ostomy appliance 10 includes a collecting bag 14 attached to the distal surface 17 of the carrier sheet 12 at attachment 30. In one embodiment, the collecting bag 14 is detachably attached to the distal surface 17 of the carrier sheet 12. In one embodiment, a first coupling half (not shown) is arranged on the collecting bag 14 and a second coupling half (not shown) is arranged on the distal surface 17 of the carrier sheet 12. In one embodiment, the first coupling half comprises an adhesive ring and the second coupling half comprises an adhesive or non-adhesive ring-formed flange adapted to receive the adhesive ring of the first coupling half. Other types of coupling systems conventional to ostomy appliances are contemplated to be equally applicable and acceptable with an ostomy appliance according to the present disclosure.

The collecting bag 14 comprises a front wall on the distal side and a rear wall on the proximal side. These walls are made of gas- and liquid impermeable foil-material (for example of polyethylene (PE), polyvinyl-chloride (PVC) or ethylene-vinyl-acetate (EVA)) that is welded around the edges or the rim so as to form a pouch defining a waste collection chamber. The bag may be welded only partly around the rim so that an opening for emptying the bag can be provided at the bottom of the bag. In that case, the bag may be provided with means for closing that opening. The waste inlet opening is provided in the rear wall and placed in the upper part of the collecting bag so that when a user stands up, the waste inlet opening will be above the midline of the collecting bag. This leaves a larger collecting volume below the waste inlet opening. Thus, a top of the collecting bag is defined as the portion of the bag closest to the waste inlet opening, and a bottom is defined as the opposite portion of the bag.

Prior to application of the ostomy appliance to the skin, a protective release liner (not shown) can cover the proximal surface of the first adhesive material in order to ensure that the properties of the adhesive material are preserved and that the adhesive surface is not laid open until just before use. Suitable release liners include a siliconized or fluorinated release liner, such as a siliconized or fluorinated craft paper, polyethylene, polypropylene or polyethylene terephthalate film. In one embodiment, the release liner is a siliconized polyethylene film, such as medium density polyethylene from the company Huhtamaki.

In one embodiment, the through-going hole 13 is a relatively small opening allowing for individual customization according to the size and shape of the user's unique stoma. In one embodiment, the through-going hole 13 is a relatively larger opening being provided at manufacture. In another embodiment, a customized size and shape of the through-going hole 13 to fit an individual's stoma is provided at manufacture.

In embodiments, the carrier sheet 12 comprises a blown film based on one or more Ethylene Vinyl Acetate (EVA) materials, one or more Thermoplastic Polyurethane Elastomer (TPU) based materials and one or more Polyethylene (PE) materials or blends thereof.

In embodiments, the first adhesive material 18 can comprise polyisobutylene, styrene-isoprene-styrene and hydrocolloids such as, but not limited to, the types of adhesives disclosed in WO 99/11302.

In embodiments, the first adhesive material 18 is a pressure sensitive adhesive composition, such as one described in European patent EP1541180, comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. Another suitable first adhesive material is described in WO2009/006901.

In embodiments, the second material 20 is a material that is configured to dissipate in response to being exposed to stomal fluids. In embodiments, the second material 20 is an adhesive material. In embodiments, the adhesive material of the second material 20 comprises one or more of the adhesive types of the first adhesive material 18 as described above. Handling fewer different types of materials, such as adhesive materials, during manufacture of the ostomy appliance, ensures lower complexity and lower costs of the manufacturing procedures.

In one embodiment, the second material 20 is an adhesive material being identical to the first adhesive material 18. This ensures low complexity in manufacturing and is envisioned to provide direct correlation between breakdown-levels of the first adhesive material 18 and of the second adhesive material 20. In other words, the rate of breakdown of the second adhesive material 20 will be the same as the rate of breakdown of the first adhesive material 18 when subjected to the same stomal fluids.

The factors influencing when the signal generator 22 sets off the indicator signal will therefore be reduced to a question of dimensions and how the second adhesive material and the signal generator 22 are configured in relation to each other.

A preferred level of security, in terms of how soon before the first adhesive material 18 fails an indication signal is desired, can therefore be straightforwardly selected by dimensioning and configuring the second adhesive material 20 in relation to the signal generator 22 according to the different embodiments of this disclosure.

In one embodiment, the second material 20 comprises a material that dissipates very easily when subjected to fluids, including stomal fluids. In one embodiment, the second material 20 has a second dissipation rate when subjected to stomal fluids that is substantially higher than a first dissipation rate of the first adhesive material 18, such as a factor of ten or higher.

In embodiments, the second material 20 is provided such as to form a polymer matrix composition. In embodiments, the polymer matrix composition is soluble in liquids and/fluids, such as stomal fluids and water. The solubility of the polymer matrix, or rate of dissipation, can be selected in accordance with the principles presented above.

In embodiments, the signal generator 22 is provided as a substance or compound of two or more substances. In embodiments, the substance, or substances, forming the signal generator 22 is located on the distal surface 17 of the carrier sheet 12 and proximal to the polymer matrix composition of the second material 20. In one embodiment, the substance, or substances, forming the signal generator 22 is embedded, i.e. enclosed in the surrounding mass of the polymer matrix composition of the second material 20.

In one embodiment, the substance of the signal generator 22 comprises a colorant. The colorant substance is dissolvable in liquids and/or fluids, such as stomal fluids reaching the colorant substance. Thereby, the colorant substance will color the stomal output and the colored output dropping into the collecting bag provides the indicator signal, instructing the user to change to a new appliance. Examples of suitable colorants include, but are not limited to, food colors and other soluble dyes.

Alternatively, or additionally, the signal generator 22 is adapted to provide the indicator signal as a change in the visual characteristics of the second material 20 or of the distal surface 17 of the carrier sheet 12. This can include providing the signal generator 22 as a colorant that dissolves into the polymer matrix of the second material 20, or dissolves into the distal surface 17 of the carrier sheet 12 when subjected to liquids and/or fluids.

In one embodiment, the signal generator 22 comprises a sticker indicator 40 (illustrated in FIG. 4). In one embodiment, the sticker indicator 40 contains a substance that changes color when subjected to liquids and/or fluids. In one embodiment, the sticker indicator 40 is provided on a portion of the distal surface 17 of the carrier sheet 12 located in a second zone 28 radially outward of an attachment 30 of the collecting bag 14 to the distal surface 17 of the carrier sheet 12, seen in relation to a central longitudinal axis 34 extending through the through-going hole.

Alternatively, or additionally, the signal generator 22 is adapted to provide the indicator signal as a change in the tactile characteristics of the second material 20 or of the distal surface 17 of the carrier sheet 12. This can include providing a signal generator 22 substance as a swellable material capable of taking up moisture from the stomal output and engaging with the polymer matrix of the second material 20, or with the distal surface 17 of the carrier sheet 12. When the swellable material takes up moisture from the stomal fluids it increases in volume. The increased volume of the material provides an easily detectable tactile indication signal that an upcoming change of appliance is near. Particularly, it provides the user or health care professional with an option of detecting the indicator signal by palpating the portion of the appliance in the peristomal area. Suitable swellable materials include hydrocolloids such as CMC and pectin.

These options facilitate detection of the indicator signal at more than one location, including at, or near, the stoma, on the carrier sheet 12 and in the collecting bag. The options can be applied individually or further advantageously in combinations.

In embodiments, the substance of the signal generator 22 is adapted to take up moisture and turn into a gel-like material when subjected to liquids and/or fluids. The material can be provided in dry form at manufacture and then take up moisture and turn into the gel-like material when subjected to stomal fluids. The gel-like material can be adapted to increase in volume or to alternatively substantially maintain its volume, even after moisture uptake. The gel-like material provides another option for producing a tactilely (and visually) indicator signal that is easily detectable for the user. In one embodiment, the substance of the signal generator 22 is provided in a ring shape surrounding the through-going hole 13.

In embodiments, the signal generator 22 is adapted to provide an indicator signal when the dissipation of the second material 20 reaches a pre-defined threshold value, or level. The pre-defined threshold value, or level, can be selected in accordance with the principles presented above.

In one embodiment, the signal generator 22 comprises an electronic component. In one embodiment, the electronic component is adapted to be powered by a battery. In one embodiment, the electronic component is adapted to be powered by a piezoelectric element.

In one embodiment, the signal generator 22 comprises an indicator signal emitter. In one embodiment, the signal generator 22 is adapted to provide the indicator signal as a sound signal. In one embodiment, the signal generator 22 is adapted to provide the indicator signal as an optical signal. In one embodiment, the signal generator 22 is adapted to provide the indicator signal as a radio signal. In embodiments, the signal generator 22 comprises an NFC (Near Field Communication) unit. In embodiments, the NFC unit is adapted to communicate with a portable device, such as, but not limited to, a smartphone, a smartwatch or a tablet and configured to communicate the signal indicating upcoming change of appliance to the user via the portable device.

In one embodiment, the signal generator 22 includes a sensor. In one embodiment, the sensor is sensible to liquids and/or fluids. In one embodiment, the sensor is sensible to inflow of light to the sensor. In one embodiment, the sensor is sensible to the presence of material on a surface of the sensor. In one embodiment, the sensor is sensible to pressure. In one embodiment, the sensor is sensible to changes in relative humidity.

Embodiments provide an ostomy appliance comprising a signal generator adapted to give a user or a health care professional a warning in time to change the appliance before leakage occurs by predetermining leakage or potential leakage of stomal fluids. A plurality of suitable options for providing a signal generator according to the present disclosure have been disclosed. Embodiments further provide ostomists with an improved possibility of avoiding troublesome and embarrassing leakage incidents, leading to an improved feeling of security and increased quality-of-life wearing an ostomy appliance as presented. Embodiments further provide an ostomy appliance comprising a leakage warning signal generator provided on a distal surface of the base plate, i.e. on the side of the base plate facing away from the user's skin surface, thereby facing away from the surface of the base plate where leakage normally occurs. This provides for an ostomy appliance having a predictive leakage indicator in contrast to a reactive leakage indicator, which in turn saves the user of the burden of leakage occurring unexpectedly.

Embodiments, and features of the various exemplary embodiments described in this application, may be combined with each other ("mixed and matched"), unless specifically noted otherwise.

What is claimed is:

1. A method of providing a signal to alert an ostomate of an imminent leakage of stoma fluids from an ostomy device worn by the ostomate, the method comprising:

providing an ostomy appliance comprising a carrier sheet having a first adhesive deposited on a proximal side of the carrier sheet and adapted to secure the ostomy appliance to skin of the ostomate, a second material deposited on a distal side of the carrier sheet, a hole formed through the first adhesive and the carrier sheet and the second material with the hole adapted to fit the ostomy appliance around a stoma of the ostomate, a connector coupling disposed on the distal side of the carrier sheet and adapted to secure an ostomy bag around the hole, and a signal generator located on the distal side of the carrier sheet and in contact with the second material;

determining a first dissipation rate of the first adhesive that is indicative of at least one of a reduction in load-carrying of the first adhesive and a reduction in liquid barrier of the first adhesive due to contact of the first adhesive with stomal output;

dimensioning a second dissipation rate of the second material to be higher than the first dissipation rate of the first adhesive;

locating the signal generator between the hole and the connector coupling for exposing the signal generator to an interior of the ostomy bag secured to the ostomy appliance and locating an indicator outside of the ostomy bag by positioning the indicator between connector coupling and an outermost perimeter of the carrier sheet; and providing a warning to the ostomate with the indicator located outside of the ostomy bag of a potential leakage of the stomal output relative to the first adhesive on the proximal side of the carrier sheet based on a dissipation of the second material due to the stomal output sensed by the signal generator exposed to the interior of the ostomy bag.

2. The method of claim 1, further comprising:
locating the signal generator between the carrier sheet and the second material.

3. The method of claim 1, further comprising:
locating the signal generator on the distal side of the carrier sheet and completely covering the signal generator with the second material.

4. The method of claim 1, wherein the second material is a second adhesive, the method further comprising:
attaching the generator to a distal surface of the carrier sheet and between the carrier sheet and the second adhesive.

5. The method of claim 1, further comprising:
providing a visual change to the indicator as the warning to the ostomate of the potential leakage of the stomal output relative to the first adhesive.

6. The method of claim 1, further comprising:
providing a tactile change to the indicator as the warning to the ostomate of the potential leakage of the stomal output relative to the first adhesive.

7. The method of claim 1, further comprising:
providing a sound from the indicator as the warning to the ostomate of the potential leakage of the stomal output relative to the first adhesive.

8. The method of claim 1, wherein the connector coupling further comprises a coupling flange on the ostomy appliance that is adapted to removably attach with a mating flange on the ostomy bag.

9. The method of claim 1, wherein the connector coupling further comprises an adhesive coupling ring adapted to removably attach with a second-half adhesive coupling ring applied to the ostomy bag.

10. The method of claim 1, further comprising:
locating the indicator away from the stomal output to be collected inside of the ostomy bag during use.

11. The method of claim 1, further comprising:
formulating the second material to breakdown due to the stomal output before the first adhesive breaks down from the stomal output.

12. The method of claim 1, wherein dimensioning the second dissipation rate of the second material to be higher than the first dissipation rate of the first adhesive further comprises:
predicting a breakdown level of the first adhesive indicating reduced liquid barrier properties of the first adhesive based on the higher second dissipation rate of the second material; and
providing the warning to the ostomate, during use and before the stomal output leaks between the first adhesive and the skin of the ostomate, with a color change of the indicator.

* * * * *